(12) United States Patent
Cinader, Jr. et al.

(10) Patent No.: US 7,762,815 B2
(45) Date of Patent: Jul. 27, 2010

(54) METHOD OF MAKING AN INDIRECT BONDING TRAY FOR ORTHODONTIC TREATMENT

(75) Inventors: David K. Cinader, Jr., Yorba Linda, CA (US); James D. Cleary, Glendora, CA (US)

(73) Assignee: 3M Innovative Properties Co., St. Paul, MN (US)

( * ) Notice: Subject to any disclaimer, the term of this patent is extended or adjusted under 35 U.S.C. 154(b) by 1160 days.

(21) Appl. No.: 11/128,445

(22) Filed: May 13, 2005

(65) Prior Publication Data
US 2006/0257821 A1 Nov. 16, 2006

(51) Int. Cl.
A61C 11/00 (2006.01)
(52) U.S. Cl. .................................... 433/213
(58) Field of Classification Search .............. 433/2, 433/3, 8, 9, 24, 213, 223; 29/896.11
See application file for complete search history.

(56) References Cited

U.S. PATENT DOCUMENTS

| | | | |
|---|---|---|---|
| 4,551,096 A * | 11/1985 | Dellinger | ................ 433/24 |
| 4,657,508 A | 4/1987 | Dellinger | |
| 5,015,180 A | 5/1991 | Randklev | |
| 5,172,809 A | 12/1992 | Jacobs et al. | |
| 5,354,199 A | 10/1994 | Jacobs et al. | |
| 5,429,229 A | 7/1995 | Chester et al. | |
| 5,971,754 A | 10/1999 | Sondhi et al. | |
| 6,123,544 A | 9/2000 | Cleary | |
| 6,302,688 B1 | 10/2001 | Jordan et al. | |
| 2003/0163291 A1 | 8/2003 | Jordan et al. | |
| 2004/0166462 A1 | 8/2004 | Phan et al. | |
| 2004/0219471 A1 | 11/2004 | Cleary et al. | |
| 2004/0229185 A1 | 11/2004 | Knopp | |
| 2004/0253562 A1 * | 12/2004 | Knopp | ................ 433/24 |
| 2005/0074716 A1 | 4/2005 | Cleary et al. | |
| 2005/0133384 A1 | 6/2005 | Cinader et al. | |
| 2005/0244790 A1 * | 11/2005 | Kuperman | ................ 433/213 |

FOREIGN PATENT DOCUMENTS

WO      WO 02/089693      11/2002

OTHER PUBLICATIONS

Pending U.S. Appl. No. 11/098,317, filed Apr. 4, 2005.
Pending U.S. Appl. No. 10/967,797, filed Oct. 18, 2004.
Pending U.S. Appl. No. 11/098,716, filed Apr. 4, 2004.

* cited by examiner

*Primary Examiner*—Cris L Rodriguez
*Assistant Examiner*—Sunil K Singh
(74) *Attorney, Agent, or Firm*—Pamela L. Stewart (57) ABSTRACT

An indirect bonding tray for use in applying and bonding orthodontic appliances to a patient's teeth is made by providing a replica of the patient's dentition including replicas of the patient's teeth. A guide is provided on each replica tooth in a location corresponding to the ultimate intended location of the orthodontic appliance on the patient's teeth. Each guide has a receptacle for receiving an orthodontic appliance, and serves to ensure that the respective orthodontic appliance is placed in its proper, intended position on the replica tooth. A tray is then formed over the replica teeth and the appliances for subsequent use in bonding the appliances to the patient's teeth.

14 Claims, 4 Drawing Sheets

METHOD OF MAKING AN INDIRECT BONDING TRAY FOR ORTHODONTIC TREATMENT

BACKGROUND OF THE INVENTION

1. Field of the Invention

This invention relates to an indirect bonding tray that is used for placing orthodontic appliances on the surfaces of a patient's teeth. More particularly, the present invention is directed toward a method and an assembly for making an indirect bonding tray.

2. Description of the Related Art

Orthodontic treatment involves movement of malpositioned teeth to desired locations in the oral cavity. Orthodontic treatment can improve the patient's facial appearance, especially in instances where the teeth are noticeably crooked or where the jaws are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and an archwire is placed in the slot of each bracket. The archwire forms a track to guide movement of teeth to desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly referred to collectively as "braces".

In many types of orthodontic techniques, the precise position of the appliances on the teeth is an important factor for helping to ensure that the teeth move to their intended final positions. For example, one common type of orthodontic treatment technique is known as the "straight-wire" technique, where the archwire lies in a horizontal plane at the conclusion of treatment. Consequently, if a bracket is attached to the tooth at a location that is too close to the occlusal or outer tip of the tooth, the orthodontist using a straight-wire technique will likely find that the tooth in its final position is unduly intruded. On the other hand, if the bracket is attached to the tooth at a location closer to the gingiva than is appropriate, it is likely that the final position of the tooth will be more extruded than desired.

In general, orthodontic appliances that are adapted to be adhesively bonded to the patient's teeth are placed and connected to the teeth by either one of two techniques: a direct bonding technique, or an indirect bonding technique. In the direct bonding technique, the appliance and adhesive are grasped with a pair of tweezers or other hand instrument and placed by the practitioner on the surface of the tooth in an approximate desired location. Next, the appliance is shifted along the surface of the tooth as needed until the practitioner is satisfied with its position. Once the appliance is in its precise, intended location, the appliance is pressed firmly onto the tooth to seat the appliance in the adhesive. Excess adhesive in areas adjacent the base of the appliance is removed, and the adhesive is then allowed to cure and fix the appliance firmly in place.

While the direct bonding technique described above is in widespread use and is considered satisfactory by many, there are shortcomings that are inherent with this technique. For example, access to surfaces of malposed teeth may be difficult. In some instances, and particularly in connection with posterior teeth, the practitioner may have difficulty seeing the precise position of the bracket relative to the tooth surface. Additionally, the appliance may be unintentionally dislodged from its intended location during the time that the excess adhesive is being removed adjacent the base of the appliance.

Another problem associated with the direct bonding technique described above concerns the significant length of time needed to carry out the procedure of bonding each appliance to each individual tooth. Typically, the practitioner will attempt to ensure that each appliance is positioned in its precise, intended location before the adhesive is cured, and some amount of time may be necessary before the practitioner is satisfied with the location of each appliance. At the same time, however, the patient may experience discomfort during the procedure and have difficulty in remaining relatively motionless, especially if the patient is an adolescent. As can be appreciated, there are aspects of the direct bonding technique that can be considered a nuisance for both the practitioner and for the patient.

Indirect bonding techniques avoid many of the problems noted above. In general, indirect bonding techniques known in the past have involved the use of a placement device or transfer tray having wall sections with a shape that matches the configuration of at least part of the patient's dental arch. Often, the tray has a generally "U"-shaped channel for receiving a number of teeth simultaneously. A set of appliances such as brackets are releasably connected to the tray at certain, predetermined locations within the channel.

During the use of orthodontic transfer tray for indirect bonding, an adhesive is typically applied to the base of each appliance by the orthodontist or a staff member. The tray is then placed over the patient's teeth and remains in place until such time as the adhesive hardens. Next, the apparatus is detached from the teeth as well as from the appliances, with the result that all of the appliances previously connected to the tray are now bonded to respective teeth at their intended, predetermined locations.

In more detail, one method of indirect bonding of orthodontic appliances using the transfer tray described above includes the steps of taking an impression of each of the patient's dental arches and then making a replica plaster or "stone" model from each impression. Next, the appliances are bonded to the stone models at desired locations. Optionally, the bonding adhesive can be a chemical curing adhesive (such as Concise brand adhesive from 3M) or a light-curable adhesive (such as Transbond XT brand adhesive or Transbond LR brand adhesive from 3M). Optionally, the brackets may be adhesive precoated brackets such as those described in U.S. Pat. Nos. 5,015,180, 5,172,809, 5,354,199 and 5,429,229.

The transfer tray is then made by placing a matrix material over the model as well as over the appliances placed in the model. For example, a plastic sheet matrix material may be held by a frame and exposed to radiant heat. Once the plastic sheet material has softened, it is placed over the model and the appliances. Air in the space between the sheet material and the model is then evacuated, and the plastic sheet material assumes a configuration that precisely matches the shape of the replica teeth of the stone model and attached appliances.

The plastic sheet matrix material is then allowed to cool and harden to form a tray. The tray and the appliances (which are embedded in an interior wall of the tray) are then detached from the stone model. If the cured adhesive that was used to bond the appliances to the stone model remains on the base of the appliances after detachment from the stone model, the adhesive serves as a "custom" base having a concave contour that precisely replicates the convex contour of the previous attachment location of the stone model, as well as the convex configuration of the intended mounting location of the appliances on the patient's teeth.

Once the patient has returned to the practitioner's office, a quantity of adhesive is placed on the base of each appliance, and the tray with the embedded appliances is then placed over the matching portions of the patient's dental arch. Since the configuration of the interior of the tray closely matches the respective portions of the patient's dental arch, each appliance is ultimately positioned on the patient's teeth at precisely the same location that corresponds to the previous location of the same appliance on the stone model.

In recent years, many improvements have been made in the field of indirect bonding. For example, U.S. Pat. No. 5,971,754 describes a two-component indirect bonding adhesive with a relatively fast curing time that reduces the length of time that the tray must be firmly held against the patient's teeth. U.S. Pat. No. 6,123,544 describes a transfer tray that receives movable arms for placing appliances on the patient's teeth once the tray is positioned in the oral cavity. Published U.S. patent application entitled "METHOD AND APPARATUS FOR INDIRECT BONDING OF ORTHODONTIC APPLIANCES" (U.S. Publication No. 2004-0219471, published on Nov. 4, 2004), describes among other things a transfer apparatus with an improved matrix material for releasably holding appliances in place. Published U.S. patent application entitled "APPARATUS FOR INDIRECT BONDING OF ORTHODONTIC APPLIANCES AND METHOD OF MAKING THE SAME" (U.S. Publication No. 2005-0074716-A1, Apr. 7, 2005 describes among other things a transfer apparatus that includes at least one appliance having a base with a contour that is a replica of a contour of a portions of the patient's tooth structure, and a bonding composition on the base for bonding to the patient's tooth structure.

Indirect bonding techniques offer a number of advantages over direct bonding techniques. For one thing, and as indicated above, it is possible to bond a plurality of appliances to a patient's dental arch simultaneously, thereby avoiding the need to bond each appliance in individual fashion. In addition, the transfer apparatus helps to locate the appliances in their proper, intended positions such that adjustment of each appliance on the surface of the tooth before bonding is avoided. The increased placement accuracy of the appliances that is often afforded by indirect bonding techniques helps ensure that the patient's teeth are moved to their proper, intended positions at the conclusion of treatment.

However, the ultimate location of the appliances on the patient's teeth during an indirect bonding procedure is determined by the earlier, temporary location of the appliances on the replica teeth. Consequently, it is important to ensure that the appliances are precisely placed on the replica teeth at the correct, pre-determined locations. The above-mentioned U.S. Pat. No. 5,971,754 describes a method of marking the replica teeth with a pencil using a gauge to determine the location of the pencil mark, and the appliances are subsequently aligned by eye to the pencil mark and then visually checked to ensure accurate placement.

As alternative to manual placement of appliances, a computer controlled robotic arm may be used to grasp each appliance in sequence and place it on the associated tooth. For example, if the replica dental arch is made using digital information, a computer may be used to calculate an idealized position for each appliance on the patient's tooth, and that information can then be used in a set of instructions to control movement of the robotic arm such that the appliance is placed on the corresponding, selected location of the associated replica tooth. With this method, the use of pencil marks for visual alignment of the appliances may be avoided.

However, the use of a robotic arm to place appliances on replica teeth presents difficulties in the manufacturing process of making the trays. For example, there are a vast number of different orthodontic appliances, each having a unique shape and prescription, and the particular appliance selected will often vary from tooth to tooth, from patient to patient, and from practitioner to practitioner. Consequently, it would be a somewhat expensive task to set up an automated system for feeding the appliances to the robotic arm due to the large number of available appliances that may be needed for any particular patient. Moreover, it may be difficult to construct a set of universal jaws for the robotic arm in order to pick up each appliance, as the external shape of the various appliances may greatly differ.

SUMMARY OF THE INVENTION

The present invention is directed toward improved methods and assemblies for making an indirect bonding tray. A replica of the patient's dentition is provided, as well as a set of guides that extend over tooth structure of the replica. Each guide has a receptacle for receiving an orthodontic appliance such that the appliance is positioned over the replica tooth structure at a precise, pre-determined location.

Preferably, the guides have a shape that is at least partially complemental to the base of the appliance to be received in the guide. As a result, the practitioner can simply select the correct appliance from an inventory of appliances, and then place the appliance in the receptacle. The guide helps to position the appliance in its precise, intended location on the replica tooth. As a result, the use of manual positioning techniques or an automated robotic arm can be avoided.

In more detail, the present invention is directed in one aspect to a method of making an indirect bonding tray for orthodontic treatment. The method comprises:

providing a replica of a patient's dentition, wherein the replica includes replica tooth structure;

providing a guide on the replica tooth structure at a location corresponding to the intended location of an orthodontic appliance on the patient's tooth structure;

placing an orthodontic appliance on the replica tooth structure next to the guide; and forming a tray over the replica including the orthodontic appliance.

The present invention in another aspect is directed toward an assembly for making an indirect bonding tray for orthodontic treatment. The assembly comprises a dentition replica including a number of replica teeth, and a number of guides each connected to a corresponding tooth of the dentition replica. Each of the guides includes a receptacle. The assembly further includes a number of orthodontic appliances each received in a corresponding receptacle.

Additional aspects of the present invention are described in the paragraphs that follow and are illustrated in the accompanying drawings.

DEFINITIONS

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's cheeks or lips.

"Lingual" means in a direction toward the patient's tongue.

DETAILED DESCRIPTION OF THE PREFERRED EMBODIMENTS

Figure 1:
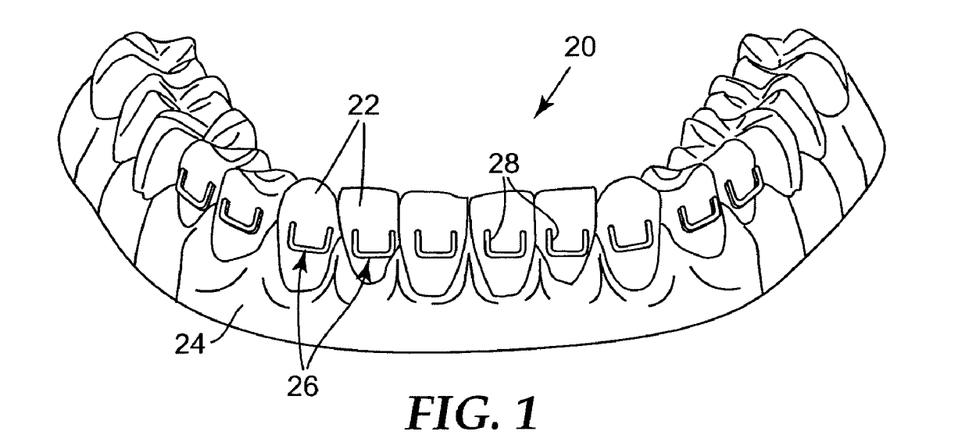
FIG. 1 is a top and front view showing a physical replica of one dental arch of an orthodontic patient, illustrating an example of a replica of a patient's tooth structure and adjacent gingival tissue as they might appear before the commencement of treatment, and additionally showing a number of placement guides extending over teeth of the replica.

A replica of a portion of a dental arch of an orthodontic patient is designated broadly by the numeral 20 in FIG. 1. For exemplary purposes, the replica 20 represents the patient's lower dental arch. However, a replica of a patient's upper dental arch may also be provided as an addition to or as an alternative to the lower dental arch replica 20 as shown. As a further option, the replica 20 may represent only a portion of the dental arch, such as a quadrant of an arch or only one or two teeth of a dental arch.

In the example illustrated, the replica 20 includes a number of replica teeth 22, each corresponding to one of the teeth of the patient's lower dental arch. In addition, the replica 20 includes replica gingival tissue 24. However, the replica gingival tissue 24 is optional, and may be provided only to an extent needed to securely hold the replica teeth 22 together.

A number of placement guides 26 extend over the dentition replica 20. In the example illustrated in FIG. 1, ten placement guides 26 are provided, each associated with one of ten of the replica teeth 22. Each of the placement guides 26 includes a central receptacle 28 disposed over the surface of the corresponding replica tooth 22.

Figure 2:
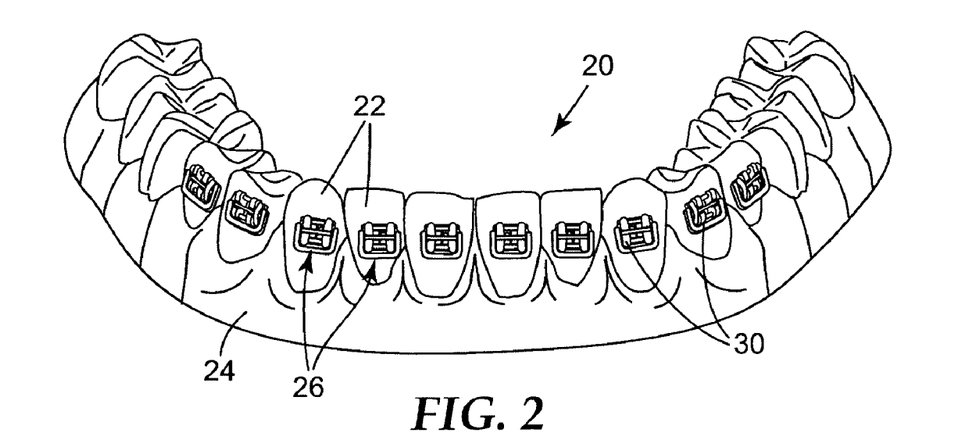
FIG. 2 is a view somewhat similar to FIG. 1 of the replica and the placement guides, and additionally illustrating a number of appliances that have been received in respective receptacles of the placement guides.
Figure 3:
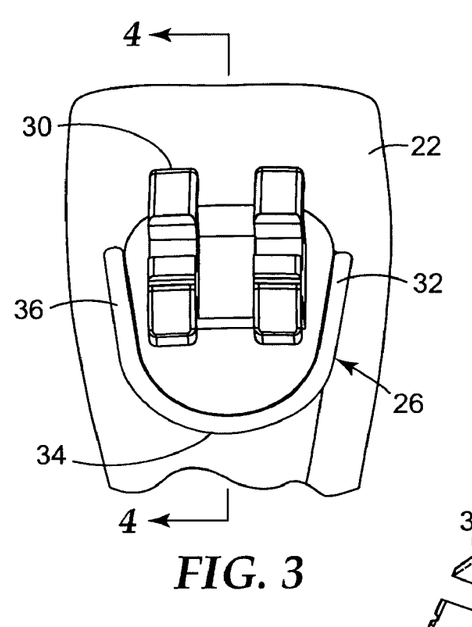
FIG. 3 is a fragmentary, enlarged front elevational view looking in a lingual direction toward one of the appliances, placement guides and replica teeth shown in FIG. 2.
Figure 4:
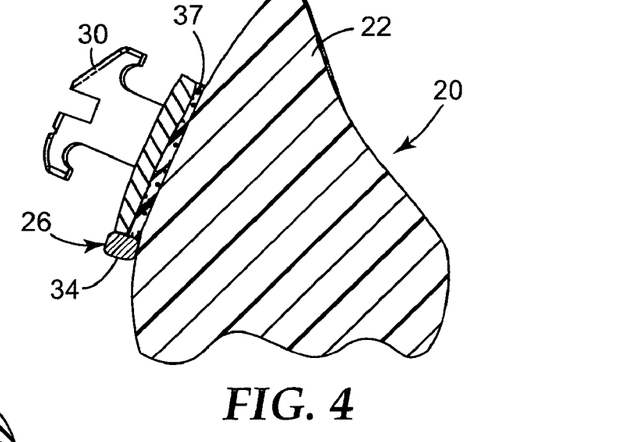
FIG. 4 is a fragmentary enlarged side view in partial section, taken along lines 4-4 of FIG. 3.

FIG. 2 is an illustration somewhat similar to FIG. 1 except showing a number of appliances 30 that have each been received in a corresponding one of the receptacles 28. FIG. 3 is an enlarged front view of one of the appliances 30, one of the placement guides 26 and one of the replica teeth 22 depicted in FIG. 2. FIG. 4 is another enlarged illustration of the same appliance 30, receptacle 28 and replica tooth 22 except this view is looking in a distal direction and is in partial cross-sectional view.

Preferably, each receptacle 28 has an inner perimeter or wall surface that is complemental in configuration to at least a portion of the base of the appliance 30 that is received in that receptacle 28. For example, and as shown in the drawings, the base of the appliance 30 may include four sides, namely a mesial side, a gingival side, a distal side and an occlusal side. The four sides of the base of the appliance 30 may be straight or generally straight and resemble a rectangle or square in a frontal view, or alternatively may be smoothly curved to form a somewhat circular, oval-shaped or tooth-shaped configuration in facial view.

In the embodiment illustrated, the placement guide 26 includes a mesial wall section 32, a gingival wall section 34 and a distal wall section 36, and the sections 32, 34, 36 are integrally connected together. The three sections 32, 34, 36 define the receptacle 28 and are positioned to closely engage the mesial side, the gingival side and the distal side respectively of the base of the appliance 30. As a consequence, when the appliance 30 is received in the receptacle 28, movement of the appliance 30 relative to the placement guide 26 is substantially prohibited in mesial, gingival and distal directions.

Alternatively, the placement guide 26 may have other constructions as well. For example, the mesial wall section 32 and the distal wall section 36 may extend along the mesial-occlusal corner and the distal-occlusal corner respectively of the appliance base. As another example, the placement guide 26 may include four sections including an occlusal section in addition to the mesial, gingival and distal sections. Preferably, this occlusal section does not extend continuously along the occlusal side of the appliance base and instead includes a gap or space to permit the passage of the extruded composition (such as adhesive) as is further explained below.

As yet another alternative, the wall sections of the placement guide 26 may comprise a series of spaced apart sections, posts or other types of protrusions that define a receptacle. However, it is preferred that the placement guides 26 have sufficient structure to receive the corresponding appliance 30 in the receptacle 28 with little, if any space between the inner wall surfaces of the placement guide 26 and the appliance 30. To this end, the receptacles 28 may vary in shape from one receptacle to the next as may be needed to matingly receive appliances having bases with different configurations.

Preferably, the height of the wall sections 32, 34, 36 in a facial direction is limited so that excess composition that is extruded from beneath the base of the appliance 30 is not directed toward certain areas of the appliance 30, such as areas beneath tiewings or areas defining an archwire slot. An example of a suitable height in a facial direction is approximately 0.5 mm greater than the thickness of the appliance base in directions along a facial-lingual reference axis.

In the embodiment shown in FIGS. 1-4, the placement guides 26 are made by applying a material to the replica 20, either after the replica 20 has been formed or as the replica 20 is formed. As one option, a rapid prototyping machine (such as a Stratasys Dimension SST (Soluble Support Technology)

from Stratasys, Inc. of Eden Prairie, Minn.) can be used to form the replica 20 as well as the various placement guides 26. First, digital data is obtained that is representative of the patient's teeth and adjacent gingival tissue. The digital data may be obtained by the use of a hand-held intra-oral scanner or other device known in the art. As another option, the digital data may be obtained by scanning an impression of the patient's teeth or a physical model (e.g., a model made of epoxy or plaster of Paris) of the patient's teeth. The digital data is then used in computer software associated with the rapid prototyping machine to make the dentition replica 20.

Preferably, the computer software also includes subprograms suitable to analyze the existing malocclusion of the patient and assist in determining the desired ultimate positions of the appliances 30 on the patient's teeth. The software may include a subprogram to assist in selecting the proper appliances for treatment of a particular malocclusion at hand. Alternatively, the software may receive input from the practitioner for selection of the desired appliances 30. Once the appliances 30 have been selected and the desired ultimate locations of the appliances 30 on the patient's teeth has been determined, the software determines the shape of the placement guides 26 and also the location of the placement guides 26 on the replica teeth 22.

Optionally, the software enables the practitioner, patient or other observer to see on a monitor or other video output a virtual representation of the patient's teeth as they should appear at the conclusion of treatment using the selected appliances 30 when placed at certain locations of the patient's teeth. Once the virtual representation of the patient's teeth at the conclusion of treatment has been observed, the software preferably enables the practitioner to make adjustments in the locations of the appliances 30 on the replica teeth or to select another appliance if desired. The software then makes any necessary correction in the shape or location of the placement guides 26 as needed. Optionally, input from the practitioner is provided in the practitioner's office and transmitted to the manufacturing facility over the internet.

An example of software for choosing appliances 30 is described in pending U.S. Patent Application Publication No. 2003/0163291, entitled "SELECTION OF ORTHODONTIC BRACKETS". As an additional option, the software includes subprograms for making custom orthodontic appliances 30 using, for example, a computer numerical control milling machine, instead of selecting appliances 30 from an existing set of appliances. As an additional option, the software may select an orthodontic archwire for subsequent placement in the slots of the appliances 30. This step serves to further reduce the patient's time that is subsequently spent in the practitioner's chair.

The rapid prototyping machine (such as the Stratasys Dimension SST apparatus described above) may also be used to form the placement guides 26 on the dentition replica 20. In the embodiment shown in FIGS. 1-4, the placement guides 26 are formed using a soluble material while the dentition replica 20 is formed using a non-soluble material. An example of a suitable soluble material is WaterWorks brand material from Stratasys, Inc. An example of a suitable non-soluble material is acrylonitrile butadiene styrene ("ABS").

A thin layer of release agent is then applied to the replica 20 and allowed to dry. An example of a suitable release agent is a water soluble polyvinyl alcohol, such as "PA0810" from PTM & W Company of Santa Fe Springs, Calif. Next, the practitioner or technician places an orthodontic appliance 30 in each receptacle 28. However, before the appliances 30 are placed in the receptacles 28, a quantity of a composition 37 (FIG. 4) is placed between each appliance 30 and the corresponding replica tooth 22.

Preferably, the composition 37 is a light-curable composition such as a light-curable adhesive, and the adhesive is coated across the base of each appliance 30. Preferably, the appliances 30 are adhesive precoated appliances that have a layer of light-curable adhesive applied by the manufacturer to the base of each appliance 30. Such adhesive coated appliances are described in U.S. Pat. Nos. 5,015,180, 5,172,809, 5,354,199 and 5,429,229. The appliances 30 may be made of any suitable material such as metal (e.g., stainless steel), ceramic (e.g., translucent polycrystalline alumina or monocrystalline alumina) or plastic (e.g., translucent polycarbonate).

If the appliances 30 are not precoated with adhesive in advance by the appliance manufacturer, the composition 37 is applied to the base of each appliance 30 immediately before placing the appliance 30 in the receptacle 28. Suitable compositions 37 include orthodontic adhesives such as composites, compomers, glass ionomers and resin-modified glass ionomers. Examples of light-curable adhesives include Transbond XT brand and Transbond LR brand adhesives from 3M Unitek Corporation. Examples of chemical curing adhesives include Concise brand adhesive and Multi-Cure brand glass ionomer cement from 3M Unitek Corporation.

Next, firm pressure is applied to each appliance 30 in order to ensure that the appliance 30 is firmly seated on the corresponding replica tooth 22. Preferably, finger pressure is applied directly to the facial side of the appliance 30 in order to seat the base of the appliance 30 against the replica tooth surface. Excess adhesive is then removed. Since the placement guide 26 as illustrated in the drawings do not include an occlusal section, most of the excess adhesive is extruded from beneath the base of the appliance 30 in an occlusal direction and toward the outer tips of the replica teeth 22.

Subsequently, the composition 37 is allowed to harden. As one example, if the appliances 30 are made of metal or other opaque material and if the composition 37 is a light-curable adhesive, it is preferable to expose the replica 20 to the curing light for a relatively long amount of time (such as 3 to 5 minutes) in order to ensure that the adhesive has sufficiently hardened.

An example of a suitable curing light for hardening light-curable adhesive is a curing chamber such as the Triad 2000 brand visible curing light system from Dentsply. Preferably, the curing chamber is sufficiently large to contain a number of replicas 20 so that the composition 37 on a number of replicas 20 can be cured simultaneously. In such a chamber, the light source and the replicas 20 preferably move relative to each other during energization of the light source to facilitate curing of each portion of the composition 37. As an alternative to the light curing chamber, a hand-held curing unit may be used, such as Ortholux XT brand curing unit from 3M Unitek Corporation.

As an additional option, the replica 20 including the replica teeth 22 may be made from a material that transmits actinic radiation. Suitable materials include epoxy resins that are transparent or translucent when hardened. Preferably, the material is optically clear. An example of a suitable epoxy is E-CAST F-82 clear epoxy resin and No. 302 (or UCE-302) hardener, from United Resin Corporation. Other suitable materials include polyesters and urethanes. The use of transparent or translucent materials is advantageous in instances where the appliances 30 are made of opaque materials, since the actinic radiation can be transmitted through the replica 20 for curing portions of the adhesive that are located adjacent the middle of the appliance base. Actinic radiation can include wavelengths in the visible range, ultraviolet range, infrared range or any combination thereof, in accordance with the type of photoinitiator contained in the adhesive.

Subsequently, the placement guides 26 are removed from the dentition replica 20 and the appliances 30. During this step, the appliances 30 remain bonded to the replica teeth 22. In this embodiment, the placement guides 26 are made of a soluble material and the replica 20 is made of an insoluble material. The placement guides 26 are removed by soaking the replica 20 and the placement guides 26 in water such that the placement guides 26 are dissolved or at least partially dissolved.

Figure 5:
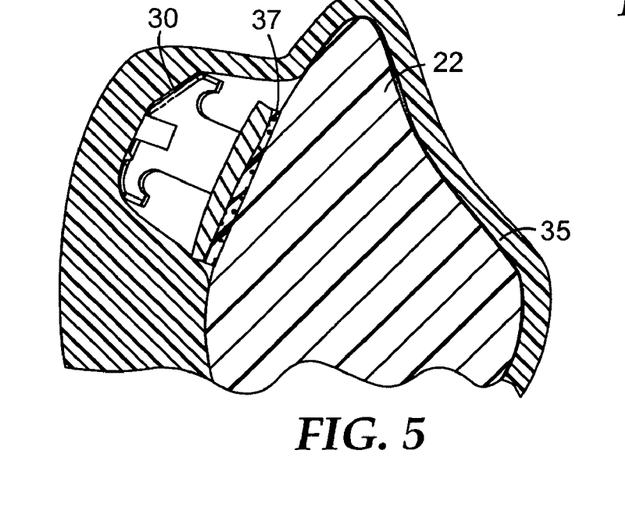
FIG. 5 is a view somewhat similar to FIG. 4 except that the placement guide has been removed from the replica tooth and a sheet of spacer material has been applied to the appliance and the replica tooth.

Next, and as shown in FIG. 5, a spacer material 35 is applied to the replica 20. The spacer material 35 preferably comprises a custom-formed material. As an example, the spacer material 35 may be dental impression putty that is pressed into place and formed by hand. An example of a suitable impression putty is "Express STD" brand impression putty from 3M Espe.

Preferably, the spacer material 35 extends over at least a majority of the facial surface area, the occlusal surface area and the lingual surface area of the replica teeth 22. However, the spacer material 35 may be omitted from contacting certain surfaces of the replica teeth 22 if desired, such as the lingual surface area of the replica teeth 22. In the illustrated embodiment, the spacer material 35 extends over the replica gingival tissue 24 as well as lingual areas of the replica teeth. Preferably, and as shown in FIG. 5, the spacer material 35 is thicker in regions located gingivally of the appliances 30 in comparison to remaining regions of the spacer material 35.

As another alternative, the spacer material 35 is formed using a rapid prototyping method. Examples of suitable rapid prototyping methods include stereolithography, thermojet printing and the like. Preferably, the digital data described above representing the shape of a portion of the patient's dental arch is used in the rapid prototyping method to make the spacer material 35.

Additionally, the spacer material 35 can be any one of a number of materials other than dental putty, such as a thermoset material. An example of an alternative material is a silicone material, such as "RTV 615" from General Electric. Other suitable materials include, for example, materials used in rapid prototyping processes, such as thermoplastics (including nylons), thermoplastic elastomers and composites (e.g., glass-filled nylons). Examples of such materials include "Sinterstation HiQ Series SLS System" brand materials (including DuraForm brand PA polyamide nylon, DuraForm Brand GF glass-filled nylon, and Somos brand 201 materials), "Viper SLA" brand materials from 3D Systems (including Dreve Otoplatik Fototec brand SL materials and Accura brand SL materials), and "Thermojet" brand materials (including Thermojet brand 88 and Thermojet brand 2000 materials).

Optionally, the spacer material 35 may be temporarily held in place on the replica 20 by use of an adhesive, such as a pressure sensitive adhesive. If the spacer material 35 is preformed, it preferably has the shape of the underlying replica dental arch when the spacer material 35 is relaxed. Alternatively, the spacer material 35 is formed to match the shape of the replica dental arch 20 when it is applied to the latter. Optionally, the spacer material 35 is coated with a layer of pressure sensitive adhesive on one side and initially connected to a sheet of release material until such time as it is needed for use.

Figure 6:
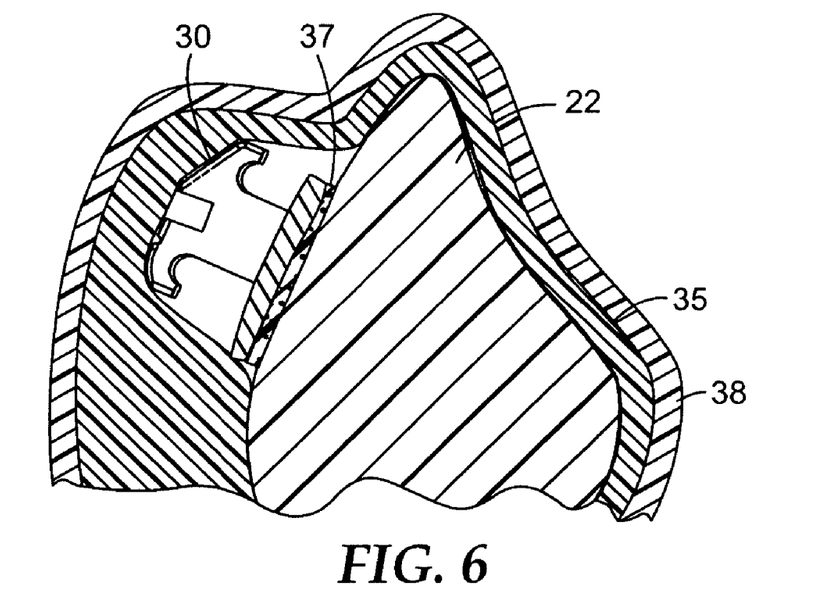
FIG. 6 is a view somewhat similar to FIG. 5, additionally showing a shell that has been formed over the spacer material.

Subsequently, a shell 38 is formed over the spacer material 35 as illustrated in FIG. 6. Preferably, the shell 38 is shaped by vacuum forming a sheet of material over the sheet of spacer material 35. A suitable material for the shell 38 is a sheet of polycarbonate such as Makrolon brand material from Bayer or Lexan brand polycarbonate from GE having a thickness of 0.06 inch. Other materials, such as polyethyleneterephthalate glycol ("PETG") may also be used. Heat is applied during the vacuum forming process in order to facilitate conformance of the sheet to the external configuration of the spacer material 35.

Once the shell 38 has hardened, the shell 38 is detached from the spacer material 35. The spacer material 35 is then detached from the replica 20 and the appliances 30 and set aside or discarded. During detachment of the spacer material 35 from the replica 20, the appliances 30 remain bonded to the replica teeth 22.

Excess portions of the shell 38 are then trimmed as desired. Next, stop members 39 (FIG. 7) are formed to facilitate subsequent positioning of the tray relative to the patient's teeth during a bonding procedure. The stop members 39 may be made by placing curable material on the replica 20 or alternatively within the channel of the shell 38. Preferably, once construction of the tray has been completed, the stop members 39 are located along the curved longitudinal axis of the tray channel and next to the bottom wall portion of the tray that defines the channel.

Figure 7:
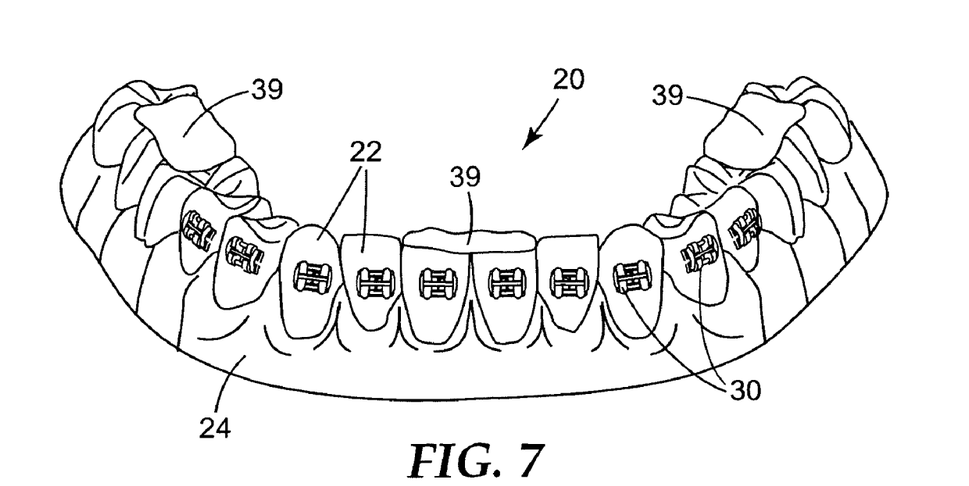
FIG. 7 is a view of the dentition replica shown in FIG. 1 after the spacer material and the shell have been detached from the replica, and additionally showing three stop members that have been placed along occlusal sections of the replica teeth.

In the embodiment illustrated in FIG. 7, three spaced-apart stop members 39 are made by placing curable material across occlusal sections of the replica dental arch 20. One stop member 39 is formed near the center of the replica dental arch 20, while the other two stop members 39 are formed near the right end and left end respectively of the replica dental arch 20. However, other constructions are possible. For example, a single stop member 39 may be provided that extends along a substantial majority of the curved longitudinal axis of the replica dental arch 20. Alternatively, two stop members 39 may be provided, each of which extends along a majority of the left quadrant and the right quadrant respectively of the replica dental arch 20 and follows the curved longitudinal axis of the arch.

Additionally, or as an alternative to occlusal stop members, one or more stop members 39 may be provided along the lingual surfaces and/or the facial surfaces of the replica dental arch 20. Lingual and facial stop members may be particularly advantageous to ensuring proper fitting and placement of the tray in instances when the patient's maloccluded teeth present diverging tooth angulations.

The stop members 39 may be made from a variety of materials. Suitable materials include, for example, an orthodontic or dental adhesive, a dental restorative material, or a bite registration material. An example of a suitable bite registration material is "Imprint" bite registration material from 3M Espe. Preferably, the stop members 39 are made of a thermosetting material that, after hardening, does not substantially soften upon contact with heat. Preferably, the stop members 39 transmit actinic radiation and retain their shape over extended periods of time.

Next, the shell 38 is placed over the replica dental arch 20 including the unhardened stop members 39. The shell 38 is pressed toward the replica arch 20 with sufficient force to deform the shape of the unhardened stop members 39 and bring the shell 38 to a desired position relative to the replica 20 as the stop members 39 are flattened. This desired position is somewhat adjacent the replica 20, but is sufficiently spaced from the replica 20 so that a quantity of matrix material may be received between the shell 38 and the replica 20 as described below. The stop members 39 are then allowed to harden. Once hardened, the stop members 39 have a gingival or tooth-facing surface that matches the occlusal surface of the facing occlusal section of the replica tooth or teeth 22.

A matrix material 40 is then applied, either to the replica 20 or to the channel of the shell 38. For example, if the matrix material 40 is relatively viscous and resembles a semi-liquid or gel, the matrix material 40 may be applied to the replica 20 as the replica 20 appears in FIG. 7, using a syringe, brush or other technique. The matrix material 40 is not shown in FIG. 7.

Figure 8:
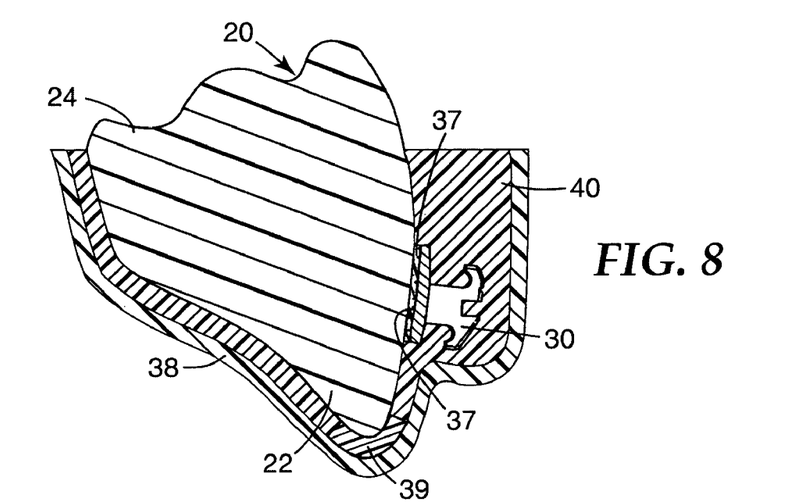
FIG. 8 is an enlarged side cross-sectional view of one of the replica teeth and one of the appliances after the placement guide has been removed, and additionally showing a transfer tray that comprises the outer shell and a matrix material located between the shell and the replica.

Alternatively, if the matrix material has a relatively low viscosity and resembles a liquid, it may be preferable to invert the shell 38 such that the open side of the channel of the shell 38 is facing upwardly as shown in FIG. 8. If the shell 38 is inverted, the shell 38 is not initially trimmed along the outermost distal sides (corresponding to the ends of the dental arch) so that the liquid matrix material 40 is contained within the shell channel.

Subsequently, the replica 20 is positioned in the shell 38 such that the matrix material 40 is received in the channel of the shell 38 and between the shell 38 and the replica 20. As shown in FIG. 8, the matrix material 40 surrounds the appliance 30 and also extends along the labial and lingual surfaces of the replica tooth 22. Moreover, the matrix material 40 extends along the bottom and side wall surfaces of the shell 38. The stop members 39 serve to properly position the shell 38 from the external surfaces of the replica teeth 22 as the matrix material 40 is received in the shell channel. The matrix material 40 is then allowed to harden.

Preferably, the matrix material 40 surrounds each appliance 30 and the entire replica arch 20 except in areas near the stop members 39, which remain in contact with the occlusal sections of the replica 20. Preferably, the matrix material 40 and the stop members 39 chemically bond to each other as the matrix material 40 has hardened, so that the stop members 39 are not unintentionally detached during the subsequent steps.

Preferably, the matrix material 40 has a relatively low viscosity before hardening so that intimate contact between the matrix material 40 and each appliance 30 is assured. In this manner, the matrix material 40 is able to substantially penetrate in various recesses, cavities and other structural features of each appliance 30 so that a secure connection between the appliance 30 and the matrix material 40 can be established. An example of a suitable matrix material having a relatively low viscosity is a silicone material such as "RTV615" silicone material from General Electric as mentioned above. The relatively low viscosity of this silicone material also assures that this material will assume a configuration that closely matches the shape of the adjacent surfaces of the replica teeth 22.

Alternatively, the matrix material 40 may comprise a dental impression material or a bite registration material. Suitable materials include polyvinylsiloxane impression material, such as Memosil 2 brand vinyl polysiloxane material from Heraeus Kulzer Inc., or Peppermint Snap brand clear bite registration material from Discus Dental. If a light-curable adhesive is to be subsequently used for bonding the appliances 30 to the patient's teeth, the matrix material 40 is preferably optically clear and transmits actinic radiation without substantial absorption.

Once the matrix material 40 has hardened, the shell 38, together with the matrix material 40 and the appliances 30, are detached from the replica 20. The use of the release agent as mentioned above helps facilitate detaching of the appliances 30 from the corresponding replica teeth 22. Excess material of the shell 38 and excess matrix material 40 are then trimmed as desired as discarded. The resultant tray (comprising the shell 38, the matrix material 40 and the stop members 39) is shown in cross-sectional view in FIG. 9 and is designated by the numeral 44.

Once the patient has returned to the office, the patient's teeth that are to receive appliances 30 are isolated using cheek retractors, tongue guards, cotton rolls, dry angles and/or other articles as needed. The teeth are then thoroughly dried using pressurized air from an air syringe. Etching solution (such as 3M Unitek Transbond XT brand etching gel) is then dabbed onto the teeth in the general area that is to be covered by the appliances 30, taking care to prevent the etching solution from flowing into interproximal contacts or engaging the skin or gingiva.

After the etching solution has remained on the selected tooth surfaces for a period of approximately thirty seconds, the solution is rinsed away from the teeth with a stream of water for fifteen seconds. The patient's teeth are then dried by the application of pressurized air from an air syringe (for example, for a time period of thirty seconds) and excess water is removed by suction. Care should also be undertaken to ensure that the saliva does not come in contact with the etched enamel surfaces. Cotton rolls and other absorbent devices are replaced as needed, again making sure that saliva does not contact the etched enamel. Air from the air syringe may then be applied to the teeth again to ensure that the teeth are thoroughly dried.

Figure 9:
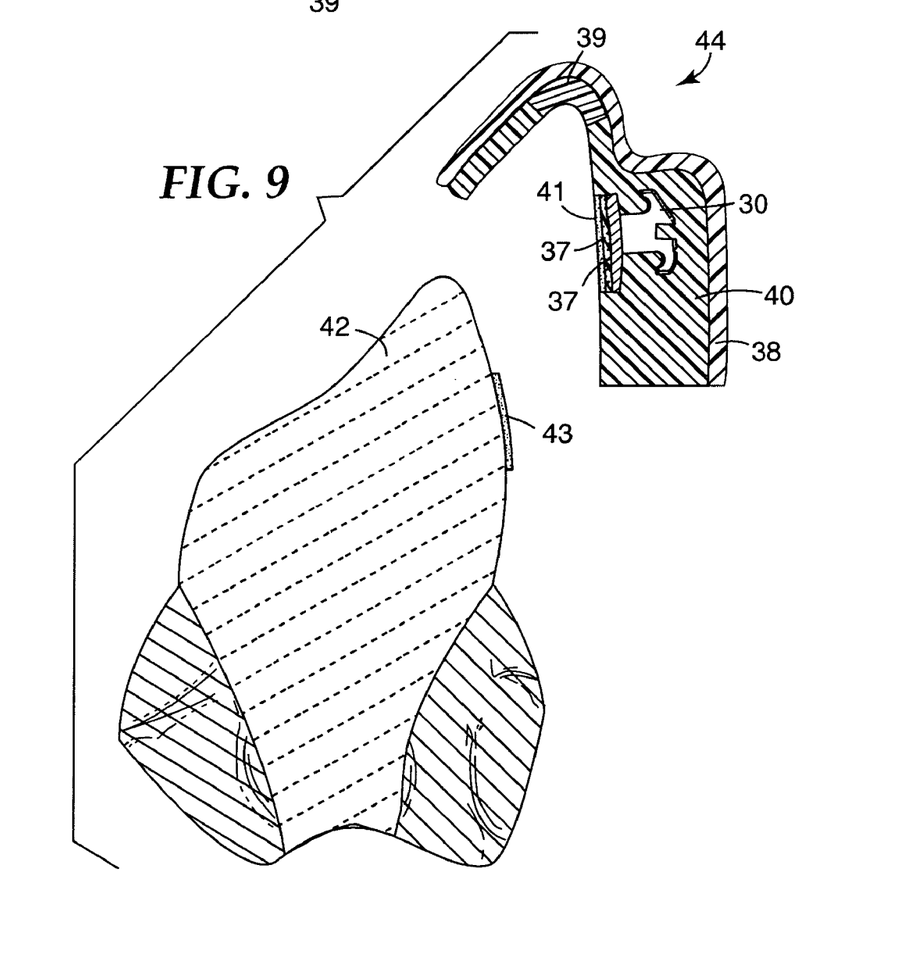
FIG. 9 is an enlarged side cross-sectional view illustrating the act of applying the transfer tray to one of the patient's teeth.

Next, a bonding adhesive is applied to the hardened composition 37 and/or the selected areas of the patient's teeth. Optionally, the adhesive is a two-component adhesive as depicted in FIG. 9. For example, the first component 41 is a Transbond brand XT primer, and the second component 43 is Transbond brand Plus self-etching primer, both from 3M Unitek. The first component 41 is applied to the hardened composition 37 and the second component 43 is applied to the area of the patient's tooth that is to receive the appliance 30. In FIG. 9, the patient's tooth is designated by the numeral 42.

After the first component 41 has been applied to the hardened composition 37 and the second component 43 has been applied to the corresponding area of the patient's tooth 42, the tray 44 is then positioned over the corresponding teeth and seated, optionally with a swinging, hinge-type motion. Since the shape of the cavity of the matrix material 40 and the stop members 39 together match the shape of the underlying teeth, the appliances 30 are simultaneously seated against the underlying teeth 42 at precisely the same locations corresponding to the previous position of the appliances 30 on the replica 20.

Preferably, the tray 44 has a shape and stiffness that is sufficient to press the appliances 30 against the teeth 42 as the adhesive cures without the application of external pressure. However, as an option, external pressure may also be applied to the occlusal and facial surfaces of the tray 44 until such time as the bonding adhesive has sufficiently hardened. For example, finger pressure may be used to firmly press the appliances 30 against the enamel surfaces of the patient's teeth 42.

Other examples of suitable two-component chemical curing adhesives include Sondhi brand Rapid-Set indirect bonding adhesive, Unite brand adhesive and Concise brand adhesive, all from 3M Unitek. Alternatively, a resin-modified glass ionomer cement may be employed.

Once the bonding adhesive has hardened, the tray 44 is carefully removed from the patient's dental arch. Preferably, the shell 38 is first separated from the matrix material 40, which remains in place over the dental arch along with the appliances 30. Next, the matrix material 40 is detached from the appliances 30. Optionally, a hand instrument such as a scaler may be used to help hold each appliance 30 against the surface of the respective tooth 42 of the patient as the matrix material 40 is peeled away from the appliances 30. However, in instances where a relatively soft matrix material is employed or otherwise readily releases from the appliances 30, the use of a scaler to help avoid fracturing the fresh adhesive bond is optional.

As another option, the shell 38 may be separated from the matrix material 40 before the bonding adhesive has hardened. This option is particularly useful when the bonding adhesive is a light-curable adhesive.

Once the matrix material 40 has been detached from the appliances 30, an archwire is placed in the slots of the appliances 30 and ligated in place. Suitable ligation devices include tiny, elastic O-rings as well as sections of wire that are tied in a loop around the appliances 30. As another option, the appliances 30 may be self-ligating appliances that include a latch for releasably engaging the archwire such as those described in U.S. Pat. No. 6,302,688 and PCT Publication No. WO02/089693.

The hardened composition 37 provides a contoured bonding surface for the base of the corresponding appliance 30. The configuration of this bonding surface closely matches the shape of the patient's tooth surface and consequently facilitates the subsequent bond (using the bonding adhesive components 41, 43) that is established between the appliance 30 and the tooth 42. The custom bonding surface reduces the likelihood that the appliances 30 will become unintentionally detached from the patient's teeth during the course of treatment.

The use of the spacer material 35 in combination with the stop members 39 in the method described above helps to provide an appropriate region for receiving matrix material 40 in the shell 38. The spacer material 35 and the stop members 39 can be shaped as needed to provide precisely the volume and configuration of region as may be desired. For example, the spacer material 35 and the stop members 39 may help ensure that a uniform thickness of matrix material is subsequently provided around the substantial extent of the tooth 42 with the exception of the areas adjacent the appliance 30 and the occlusal section of the dental arch adjacent the stop members 39.

Moreover, the use of the spacer material 35 facilitates the use of a matrix material 40 having a relatively low viscosity, such as a matrix material having a liquid consistency. The shell 38 is relatively stiff, and consequently maintains its shape during forming and hardening of the matrix material 40. The tray 44 is constructed such that the shell 38 (other than the stop members 39) does not directly contact the patient's teeth or gingival tissue. Instead, only the matrix material 40 and the stop members 39 come into contact with the patient's teeth.

Advantageously, the relatively soft matrix material 40 is flexible and can accommodate a limited amount of tooth movement. For example, the teeth 42 of the patient may have slightly shifted between the time that the impressions are taken and the time that the tray 44 is fitted in the patient's oral cavity for bonding the appliances 30. The matrix material 40 has sufficient flexibility to comply with small shifts or adjustments in the patient's tooth positions, so that the appliances 30 are properly bonded to the intended, pre-determined locations on the patient's teeth 42.

The matrix material 40 preferably has a viscosity before curing that is less than about 60,000 cp. More preferably, the matrix material 40 has a viscosity before curing that is less than about 25,000 cp. Most preferably, the matrix material 40 has a viscosity before curing that is less than about 8000 cp.

Once hardened, the matrix material 40 has a Shore A hardness that is in the range of about 10 to about 80, more preferably in the range of about 30 to about 60 and most preferably in the range of about 40 to about 50.

The stop members 39 are relatively inflexible and have a Shore A hardness that is greater than the Shore A hardness of the matrix material 40. Preferably, the stop members 39 have a Shore A hardness that is greater than about 60 and more preferably is greater than about 90.

The placement guides 26 are a significant advantage, in that time and effort associated careful, manual positioning of the appliances 30 on the replica 20 can be avoided. Moreover, when constructed using automated techniques as described above, the placement guides 26 help to avoid manual errors in positioning of the appliances 30. As an additional advantage, the matching shape of the placement guides 26 and the corresponding bases of the selected appliances 30 provides assurance that the correct appliance 30 has been placed on the proper replica tooth 22.

Figure 10:
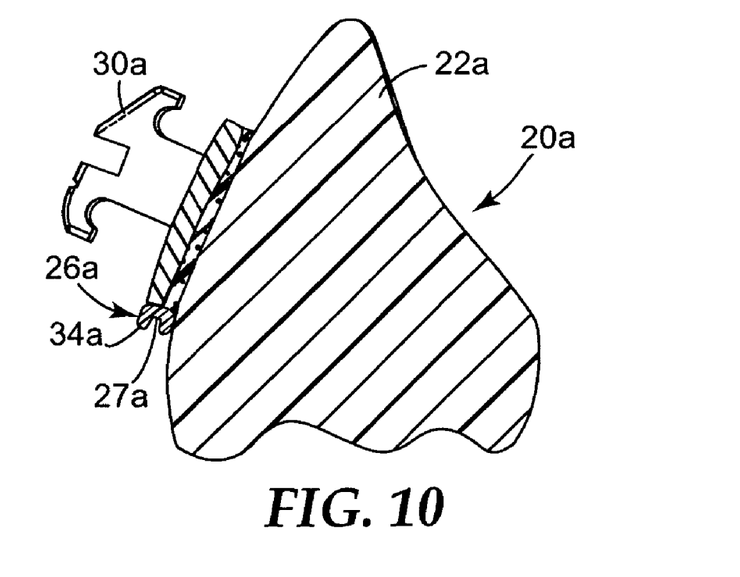
FIG. 10 is a view somewhat similar to FIG. 4 except showing a placement guide constructed in accordance with an alternate embodiment of the invention.

FIG. 10 is a view somewhat similar to FIG. 4, except illustrating a placement guide 26a that has been constructed in accordance with an alternative embodiment of the invention. In this embodiment, the placement guide 26a is made of the same material as the material of the dentition replica 20a including the teeth replicas 22a, and the dentition replica 20a and the placement guides 26a form an integral, unitary body. As one example, a stereolithography machine maybe used to print out the dentition model 20a and the placement guides 26a together.

The placement guides 26a, like the placement guides 26, include sections such as a mesial section, a distal section and a gingival section 34a. Only the gingival section 34a is shown in FIG. 10. Optionally, at least part of an occlusal section (not shown) is also provided. Each of the sections is detached from the adjacent replica tooth 22a once the appliance 30a is bonded to the replica tooth surface.

In the embodiment illustrated in FIG. 10, the mesial, gingival and distal sections of the placement guides 26a include a weakened portion 27a that comprises a relatively thin web of material. This web of material is sufficiently thin to enable the sections to be broken away from the replica tooth surface once the adjacent appliance 30a is bonded in place. For example, the weakened portions 27a may be made of a relatively brittle material that fractures when bent by the practitioner to remove the sections. As another alternative, the weakened portions 27a are sufficiently thin to be readily cut by a knife in order to detach the sections from the adjacent replica tooth 22a. In other respects, the placement guide 26a is substantially the same as the placement guides 26 described above.

A variety of other embodiments and alternative constructions are also possible. For example, additional constructions of the stop members are described in pending U.S. patent application entitled "METHOD OF MAKING INDIRECT BONDING APPARATUS FOR ORTHODONTIC THERAPY", Ser. No. 11/098,317 filed Apr. 4, 2005. Additionally, before the tray is shipped to the practitioner, a bonding composition may be applied to the base of each appliance 30, 30a by the manufacturer and then packaged in a container as described in published U.S. Patent Application No. 2005-0074716, entitled "APPARATUS FOR INDIRECT BONDING OF ORTHODONTIC APPLIANCES AND METHOD OF MAKING THE SAME". Additionally, the bonding composition of at least one appliance may differ from the bonding composition of at least one other appliance 30, 30a in the tray in terms of composition, properties or characteristics, as described in published U.S. Patent Application No. 2005/

0133384, entitled "PACKAGED ORTHODONTIC ASSEMBLY WITH ADHESIVE PRECOATED APPLIANCES", such that the bonding composition can be tailored to enhance the bond between the particular selected appliance 30, 30*a* and its intended tooth 42. Further, an archwire selected by software as described above can be placed in the slots of the appliances 30, 30*a* before the matrix material 40 is applied to the shell 38, as an alternative to placing the archwire in the slots after the tray has been removed.

As an additional option, the tray 44 may include only a single layer, instead of the two layers (comprising the matrix material 40 and the shell 38) as described above. Furthermore, the placement guides may be constructed with wall sections having a relatively small height in a facial-lingual direction, such that the placement guides need not be removed from the dentition replica and can instead remain in place during construction of the tray.

Additionally, the tray 44 as described above may be used for bonding only a single appliance 30, 30*a* to a patient's tooth. For example, a portion of the tray 44 described above may be used to bond a single appliance to a single tooth subsequent to the time that other appliances are bonded, such as in instances where access to the tooth is initially hindered by other teeth. As another example, a portion of the tray 44 described above may be used to rebond an appliance that has unintentionally debonded from the tooth, or to bond a new appliance to a tooth to replace the original appliance.

All patents, patent applications and other publications identified herein are expressly incorporated by reference into this disclosure. Moreover, a number of other variations, modifications and additions are also possible without departing from the spirit of the invention. Accordingly, the invention should not be deemed limited to the specific embodiments described in detail above, but instead only by a fair scope of the claims that follow and their equivalents.

The invention claimed is:

1. A method of making an indirect bonding tray for orthodontic treatment comprising:
   providing a replica of a patient's dentition, wherein the replica includes replica tooth structure;
   providing a guide on the replica tooth structure at a location corresponding to the intended location of an orthodontic appliance on the patient's tooth structure;
   placing an orthodontic appliance on the replica tooth structure next to the guide;
   bonding the appliance to the replica tooth structure;
   removing the guide from the replica tooth structure after the appliance has been bonded to the replica tooth structure; and subsequently
   forming a tray over the replica including the orthodontic appliance.

2. A method of making an indirect bonding tray for orthodontic treatment according to claim 1 wherein the act of removing the guide includes the act of dissolving at least part of the guide.

3. A method of making an indirect bonding tray for orthodontic treatment according to claim 1 wherein the act of removing the guide includes the act of detaching at least part of the guide.

4. A method of making an indirect bonding tray for orthodontic treatment according to claim 1 wherein the act of providing the replica and the act of providing the guide are carried out by making an integral, unitary body.

5. A method of making an indirect bonding tray for orthodontic treatment according to claim 4 wherein the act of making an integral, unitary body is carried out at least in part using a rapid prototyping method.

6. A method of making an indirect bonding tray for orthodontic treatment according to claim 1 wherein the act of providing a replica includes the act of forming a replica, and wherein the act of providing a guide includes the act of applying a material to the replica after the replica has been formed.

7. A method of making an indirect bonding tray for orthodontic treatment according to claim 6 wherein the act of forming a replica and the act of applying a material to the replica after the replica has been formed are carried out at least in part using a rapid prototyping process.

8. A method of making an indirect bonding tray for orthodontic treatment according to claim 6 wherein the act of applying a material to the replica includes the act of applying a soluble material to the replica.

9. A method of making an indirect bonding tray for orthodontic treatment according to claim 1 wherein the act of providing a guide includes the act of providing at least three wall sections for engagement with three sides of a base of the appliance.

10. A method of making an indirect bonding tray for orthodontic treatment according to claim 1 wherein the act of providing a guide includes the act of providing a guide with a receptacle for receiving a base of the appliance.

11. A method of making an indirect bonding tray for orthodontic treatment according to claim 10 wherein the receptacle has a shape that is complemental to the shape of at least three sides of the base and has an opening next to an occlusal side of the replica tooth structure.

12. A method of making an indirect bonding tray for orthodontic treatment according to claim 1 wherein the act of bonding the appliance to the replica tooth structure includes the act of applying a curable material to a region between the orthodontic appliance and the replica tooth structure.

13. A method of making an indirect bonding tray for orthodontic treatment according to claim 12 wherein the curable material is a light-curable material.

14. A method of making an indirect bonding tray for orthodontic treatment according to claim 1 wherein the replica of the patient's dentition includes a number of replica teeth, and including the act of providing a number of guides each corresponding to one of the teeth and the act of providing a number of appliances each corresponding to one of the guides.

* * * * *

UNITED STATES PATENT AND TRADEMARK OFFICE
CERTIFICATE OF CORRECTION

PATENT NO.       : 7,762,815 B2
APPLICATION NO.  : 11/128445
DATED            : July 27, 2010
INVENTOR(S)      : David K. Cinander

It is certified that error appears in the above-identified patent and that said Letters Patent is hereby corrected as shown below:

Column 3
Line 30, Delete "2005" and insert -- 2005) --, therefor.

Column 14
Line 56, After "11/098,317" insert -- , --.

Signed and Sealed this

Ninth Day of November, 2010

David J. Kappos
*Director of the United States Patent and Trademark Office*